United States Patent
Ogawa

(10) Patent No.: US 6,740,035 B2
(45) Date of Patent: May 25, 2004

(54) ULTRASONIC RECEIVING APPARATUS AND ULTRASONIC DIAGNOSING APPARATUS USING THE SAME

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/244,442

(22) Filed: Sep. 17, 2002

(65) Prior Publication Data

US 2003/0060707 A1 Mar. 27, 2003

(30) Foreign Application Priority Data

Sep. 27, 2001 (JP) .......................... 2001-296317

(51) Int. Cl.$^7$ ............................................... A61B 8/00
(52) U.S. Cl. ................................................ 600/437
(58) Field of Search ................ 600/407–471; 367/7, 11, 130, 138; 73/625, 626; 128/916

(56) References Cited

U.S. PATENT DOCUMENTS 5,566,133 A  * 10/1996 Engeler et al. ............... 367/11

OTHER PUBLICATIONS

Takahashi, et al. "Underwater Acoustic Sensor with Fiber Bragg Grating." Optical Review, vol. 4, No. 6, pp. 691–694, 1997.

Uno, et al. "Fabrication and Performance of a Fiber Optic Micro–Probe for Megahertz Ultrasonic Field Measurements." T. IEE Japan, vol. 118–E, No. 11, pp. 487–492, 1998.

* cited by examiner

Primary Examiner—Ali M. Imam
(74) Attorney, Agent, or Firm—Sughrue Mion, PLLC

(57) ABSTRACT

An ultrasonic receiving apparatus in which ultrasonic wave signals can be detected in a two-dimensional manner without necessities of electric-wiring works to a large number of very fine elements, and without increase of crosstalk and impedance. The ultrasonic receiving apparatus can be manufactured in low cost. This ultrasonic receiving apparatus includes an ultrasonic detecting element having a reception plane capable of receiving ultrasonic waves, for modulating light on the basis of ultrasonic waves applied to the respective positions of the reception plane; and a photodetector having a plurality of pixels, for detecting light output from corresponding positions of the ultrasonic detecting element.

24 Claims, 9 Drawing Sheets

ULTRASONIC RECEIVING APPARATUS AND ULTRASONIC DIAGNOSING APPARATUS USING THE SAME

BACKGROUND OF THE INVENTION

1. Field of the Invention

The present invention generally relates to an ultrasonic receiving apparatus for receiving ultrasonic waves. More specifically, the present invention is directed to an ultrasonic diagnosing apparatus to be used in medical diagnoses by receiving ultrasonic waves from biological bodies with employment of such an ultrasonic receiving apparatus.

2. Description of a Related Art

In conventional ultrasonic diagnosing apparatus, while both ultrasonic transmitting means and ultrasonic receiving means use the same systems, one-dimensional sensor array is generally employed which includes elements (vibrators) for transmitting/receiving ultrasonic waves. The vibrators are realized by using piezoelectric ceramics which is typically known as PZT (Pb(lead) zirconate titanate), or by using a polymer piezoelectric element such as PVDF (polyvinyle difluoride). Furthermore, such a one-dimensional sensor array is mechanically moved so as to acquire two-dimensional images, and those two-dimensional images are synthesized with each other, so that a three-dimensional image is obtained.

However, since there is a time lag along the mechanically moving direction of the one-dimensional sensor array in accordance with this method, tomographic images acquired at different time instants are synthesized with each other, and therefore, the synthesized image becomes blurred. As a result, this conventional method is not suitable for imaging objects to be inspected such as living bodies, for instance, in such a case where ultrasonic echo observations are carried out by employing the above-described conventional ultrasonic diagnosing apparatus.

In order to acquire a three-dimensional image having a high image quality by using ultrasonic waves, a two-dimensional sensor array capable of acquiring a two-dimensional image without being mechanically moved is necessarily required. For this reason, such a method of manufacturing a two-dimensional sensor array with employment of the above-described PZT or PVDF has been considered. In such a case where the above-described PZT or PVDF is employed so as to manufacture such a two-dimensional sensor array, elements must be processed in very fine manners, and also, a very large number of very fine elements must be connected by using wiring lines. However, it is practically difficult to process these elements in a finer manner, and also to manufacture these elements in a higher integration, as compared with the presently-available very fine processing manner and element integration method.

Also, even when these problems could be solved, there are other problems. That is, crosstalk between elements would be increased, electric impedance of elements connected by very fine wiring lines would be increased which deteriorate an S/N ratio thereof, and electrode portions of these very fine elements would be easily destroyed. Under such a circumstance, it is practically difficult to realize such a two-dimensional sensor array with employment of PZT or PVDF elements.

On the other hand, as another ultrasonic sensor without using a piezoelectric material such as PZT, an optical detecting type sensor is known in this field, by which an optical fiber is utilized and an ultrasonic wave is converted into an optical signal to be detected. As such an optical detecting type ultrasonic sensor, the below-mentioned ultrasonic sensors are reported, namely, an optical detecting type sensor using the fiber Bragg grating (will be abbreviated as an "FBG" hereinafter) described in "Underwater Acoustic Sensor with Fiber Bragg Grating" written by TAKAHASHI et al. in National Defense Academy (Japan), see OPTICAL REVIEW Vol. 4, No. 6 in 1997, p. 691–694; and an optical detecting type sensor using the Fabry-Perot resonator (will be abbreviated as an "FPR" hereinafter) described in "Fabrication and Performance of a Fiber Optic Micro-Probe for Megahertz Ultrasonic Field Measurements" written by UNO et al. in Tokyo Institute of Technology, see T. IEE Japan, Vol. 118-E, No. 11 in 1998, p. 487–492.

If such a two-dimensional sensor array is manufactured by employing these ultrasonic sensors, there are such merits that electric-wiring works to a large number of very fine elements are no longer required, and furthermore, higher sensitivities can be obtained. However, this two-dimensional sensor owns another problem that since this ultrasonic sensor itself is made in high cost, manufacturing cost of a two-dimensional sensor is increased, and also, manufacturing cost of an ultrasonic receiving apparatus using the two-dimensional sensor array is increased.

SUMMARY OF THE INVENTION

The present invention has been made to solve the above-described problems. A first object of the present invention is to provide an ultrasonic receiving apparatus capable of detecting an ultrasonic wave in a two-dimensional manner without necessities of electric-wiring works to a large number of very fine elements and without increase of crosstalk and impedance, and furthermore, to manufacture the ultrasonic receiving apparatus in low cost. Also, a second object of the present invention is to provide an ultrasonic diagnosing apparatus capable of acquiring either a two-dimensional ultrasonic image or a three-dimensional ultrasonic image by using the above-described ultrasonic receiving apparatus.

To solve the above-explained problems, an ultrasonic receiving apparatus according to one aspect of the present invention comprises: an ultrasonic detecting element having a reception plane capable of receiving ultrasonic waves, for modulating light on the basis of ultrasonic waves applied to respective positions of the reception plane; and a photodetector having a plurality of pixels, for detecting light output from corresponding positions of the ultrasonic detecting element.

Also, an ultrasonic diagnosing apparatus according to one aspect of the present invention comprises: a drive signal generating circuit for generating the drive signals; transmission means for transmitting ultrasonic waves in response to drive signals; reception means including an ultrasonic detecting element and a photodetector, the ultrasonic detecting element having a reception plane capable of receiving ultrasonic waves and modulating light on the basis of ultrasonic waves applied to respective positions of the reception plane, the photodetector having a plurality of pixels and detecting light output from corresponding positions of the ultrasonic detecting element to thereby output detection signals; signal processing means for receiving the detection signals output from the reception means to process the received detection signals; control means for controlling both generation timing of the drive signals and acquisition timing of the detection signals; image processing means for constructing image data on the basis of an output signal of the signal processing means; and an image display unit for displaying thereon an image on the basis of the image data.

According to the present invention, since the ultrasonic detecting element having the ultrasonic reception plane including positions which correspond to a plurality of pixels of the photodetector is employed, such an ultrasonic receiving apparatus can be manufactured in low cost. That is to say, this ultrasonic receiving apparatus is capable of detecting the ultrasonic waves in a two-dimensional manner without necessities of electric-wiring works to the large number of very fine elements and without increase of crosstalk and impedance. Accordingly, an ultrasonic diagnosing apparatus capable of acquiring a two-dimensional or three-dimensional ultrasonic image with better qualities can be realized by employing such an ultrasonic receiving apparatus.

BRIEF DESCRIPTION OF THE DRAWINGS

A better understanding of the present invention will become apparent from a detailed description to be read in conjunction with the accompanying drawings, in which.

DESCRIPTION OF THE PREFERRED EMBODIMENTS

Figure 1:
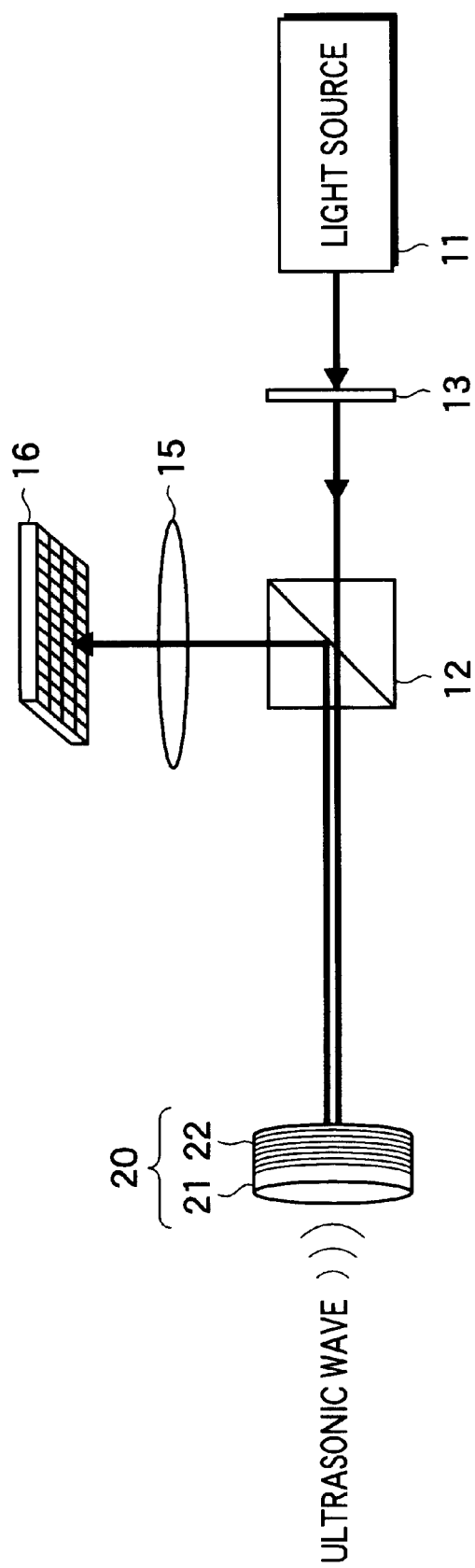
FIG. 1 is a diagram for schematically showing an arrangement of an ultrasonic receiving apparatus according to one embodiment of the present invention.

Referring now to drawings, various embodiments of the present invention will be described in detail. It should be understood that the same reference numerals are employed as those for indicating the same or similar structural elements, and explanations thereof are omitted.

FIG. 1 is a diagram for schematically showing a basic structure of an ultrasonic receiving apparatus according to one embodiment of the present invention.

This ultrasonic receiving apparatus includes a light source 11, a beam separator 12, an ultrasonic detecting element 20, a focusing system 15, and a photodetector 16. The light source 11 generates single mode laser light having a single wavelength of, for example, 500 nm to 1600 nm. The beam separator 12 is constructed by a half mirror, an optical circulator, a polarization beam splitter, or the like. This beam separator 12 may pass therethrough incident light entered from a first direction toward a second direction, and furthermore, may pass therethrough reflection light returned from the second direction toward a third direction which is different from the first direction. In this embodiment, a half mirror is employed as the beam separator 12. This half mirror 12 passes therethrough incident light and reflects thereon the reflection light which returns from a direction opposite to the incident direction so that this reflected light is propagated to a direction at substantially 90 degrees with respect to the incident direction. Alternatively, in this case, before the incident light enters the beam separator 12 along the light propagation direction, this incident light may be expanded by a beam expander 13.

The ultrasonic detecting element (multi-layer film sensor) 20 includes a base plate 21 and multi-layer film 22 stacked on the base plate 21. The ultrasonic detecting element 20 has a wave receiving plane where distortion occurs by receiving propagated ultrasonic waves. The ultrasonic detecting element 20 reflects the light which is emitted from the light source 11 and entered into the multi-layer film 22 through the beam separator 12, while modulating the light on the basis of ultrasonic waves applied to the base plate 21. The light reflected from the ultrasonic detecting element 20 is reflected by the beam separator 12 and entered into the photodetector 16 having a plurality of pixels.

The photodetector 16 corresponds to a two-dimensional array detector which is constituted by a CCD, an MOS type sensor, a plurality of PD (photodiodes) or the like. The photodetector 16 detects, for a plurality of pixels, the light which is entered from corresponding positions of the ultrasonic detecting element 20 via the beam separator 12. This photodetector 16 outputs detection signals in accordance with intensity of light at the respective pixels. In this case, the reflection light may be directly entered into the photodetector 16, or may be entered via an optical fiber or the like into the photodetector 16. Further, while the focusing system 15 such as a lens or the like is provided at a rear stage of the beam separator 12, the reflection light may be focused via this focusing system 15 onto the photodetector 16.

Figure 2:
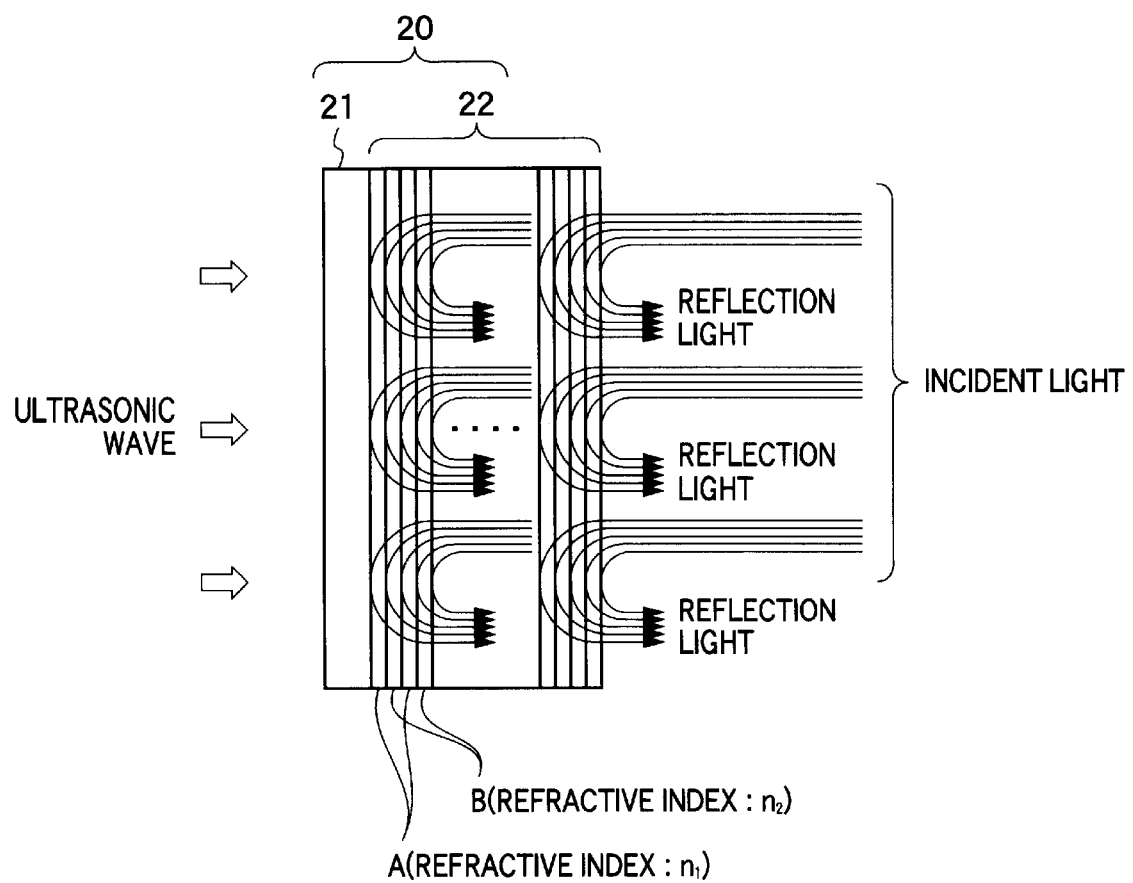
FIG. 2 is a diagram for illustratively showing an ultrasonic detecting element as shown in FIG. 1 in an enlarging mode.

Now, both a structure of the above-described ultrasonic detecting element 20 and a principle idea of detecting ultrasonic waves will be described in detail with reference to FIG. 2.

The base plate 21 is a film-shaped base plate where distortion occurs by receiving ultrasonic waves. This base plate 21 is shaped of, for example, a circle having a diameter of about 2 cm or larger. Two sorts of materials having different refractive indexes are alternately stacked on this base plate 21 so as to form the multi-layer film 22 having a Bragg grating structure. In FIG. 2, there are shown a material layer "A" having a refractive index "$n_1$" and another material layer "B" having a refractive index "$n_2$".

Assuming now that a pitch (an interval) of a periodic structure of the multi-layer film 22 is equal to "d" and a wavelength of incident light is equal to "λ", the Bragg's reflection condition is expressed by the following expression:

$$2d \cdot \sin \theta = m\lambda \tag{1}$$

where symbol "m" represents an arbitrary integer, and symbol "θ" represents an incident angle of the incident light which is measured from an incident plane.

Assuming again that this incident angle "θ" is equal to π/2, the Bragg's reflection condition is given by the following expression:

$$2d = m\lambda \quad (2)$$

The Bragg grating selectively reflects thereon such a light having a specific wavelength which satisfies the Bragg's reflection condition, and passes therethrough light having other wavelengths than the above-described specific wavelength.

When the ultrasonic waves are propagated through the ultrasonic detecting element 20, this ultrasonic detecting element 20 is distorted in accordance with the propagation of the ultrasonic waves, and therefore, the pitch "d" of the periodic structure is changed at the respective positions of the multi-layer film 22. As a result, the wavelength "λ" of the light, which is selectively reflected, is changed. In a reflection characteristic of a Bragg grating, an inclined band where reflectance is varied is present before or after a center wavelength where the reflectance becomes the highest (namely, the transmittance becomes lowest). While such a detection light having a center wavelength which is located within the range of this inclined band is entered into the multi-layer film 22, the ultrasonic waves are applied to the multi-layer film 22. As a result, intensity changes of the reflection light (otherwise the transmission light) in accordance with intensity of the ultrasonic waves at the respective positions of the ultrasonic wave receiving plane can be monitored. Since the intensity changes of the reflection light (or transmission light) are converted into intensity of ultrasonic waves, two-dimensional intensity distribution information of those ultrasonic waves can be acquired.

As a material of the above-described base plate 21, quartz glass ($SiO_2$) or optical glass such as BK7 (manufactured by Schott Glass) or the like may be employed. Also, as a substance used in the material layers "A" and "B", it is preferable to employ a combination of substances having refractive indexes which are different from each other by 10% or more. In other words, in the case of such a refractive index relationship of $n_1 < n_2$, such substances capable of satisfying $n_1 \times 1.1 \leq n_2$ are selected. This selection condition is to achieve a high reflectance at a boundary plane between the material layer "A" and the material layer "B". Also, both the material layers "A" and "B" are preferably made of such a material which can be easily expanded/compressed. This selection condition is to increase sensitivities when ultrasonic waves are applied to those material layers "A" and "B". As the combination of such substances capable of satisfying such conditions, there are a combination of $SiO_2$ and a titanium oxide ($Ti_2O_3$), another combination of $SiO_2$ and a tantalum oxide ($Ta_2O_5$) and the like. For instance, in the former case, the refractive index of $SiO_2$ is nearly equal to 1.45 and the refractive index of $Ti_2O_3$ is nearly equal to 2.0 with respect to laser light having a wavelength of 1520 nm. This fact may sufficiently satisfy the above-described condition. That is, the refractive indexes of those materials are different from each other by 10% or more.

A layer thickness (film thickness) of the material layer "A" and a layer thickness (film thickness) of the material layer "B" are preferably selected to be substantially ¼ of the wavelength "λ" of the light which is entered into the multi-layer film 22. In this case, an expression "film thickness" implies an optical distance which is expressed by a product of a refractive index "n" of a material layer and a thickness "t" of the material layer. In other words, "n·t=λ/4" may constitute the condition. As a consequence, the pitch of the periodic structure of the multi-layer film 22 becomes substantially ½ of the wavelength of the incident light, and the multi-layer film 22 can selectively reflect thereon the light having such a wavelength satisfying the above-described expression (2) of the Bragg's reflection condition and pass therethrough the light having other wavelengths than the above-described wavelength.

Alternatively, while some material layers "A" and "B" each having a layer thickness of substantially λ/4 are alternatively stacked with each other, some material layers "A" and "B" each having a layer thickness of substantially λ/2 may be intermittently stacked.

The above-mentioned material layers "A" and "B" are stacked on the substrate 21 in such a manner that multiple layers (for example, 100 layers) of each of those materials are formed thereon by way of a vapor deposition method, a sputtering method, or the like.

In connection with the above-described principle idea, a simulation was made under the following condition. In this simulation, $SiO_2$ was used as the base plate, and both $SiO_2$ and $Ti_2O_3$ were employed as the material layers. When laser light was entered into a multi-layer film sensor having a total number of 200 material layers (100 layers for each material), the below-mentioned results could be obtained. That is, an inclination of reflectance with respect to a change in wavelengths of incident light was 2.8 dB/0.01 nm at the reflectance of 25%.

Thus, when a total layer number of the multi-layer film is increased, the reflectance becomes higher, and also, the reflectance changes steeply with respective to a change in the wavelengths of incident light, so that the sensitivity of the ultrasonic detecting element 2 can be increased.

Figure 3:
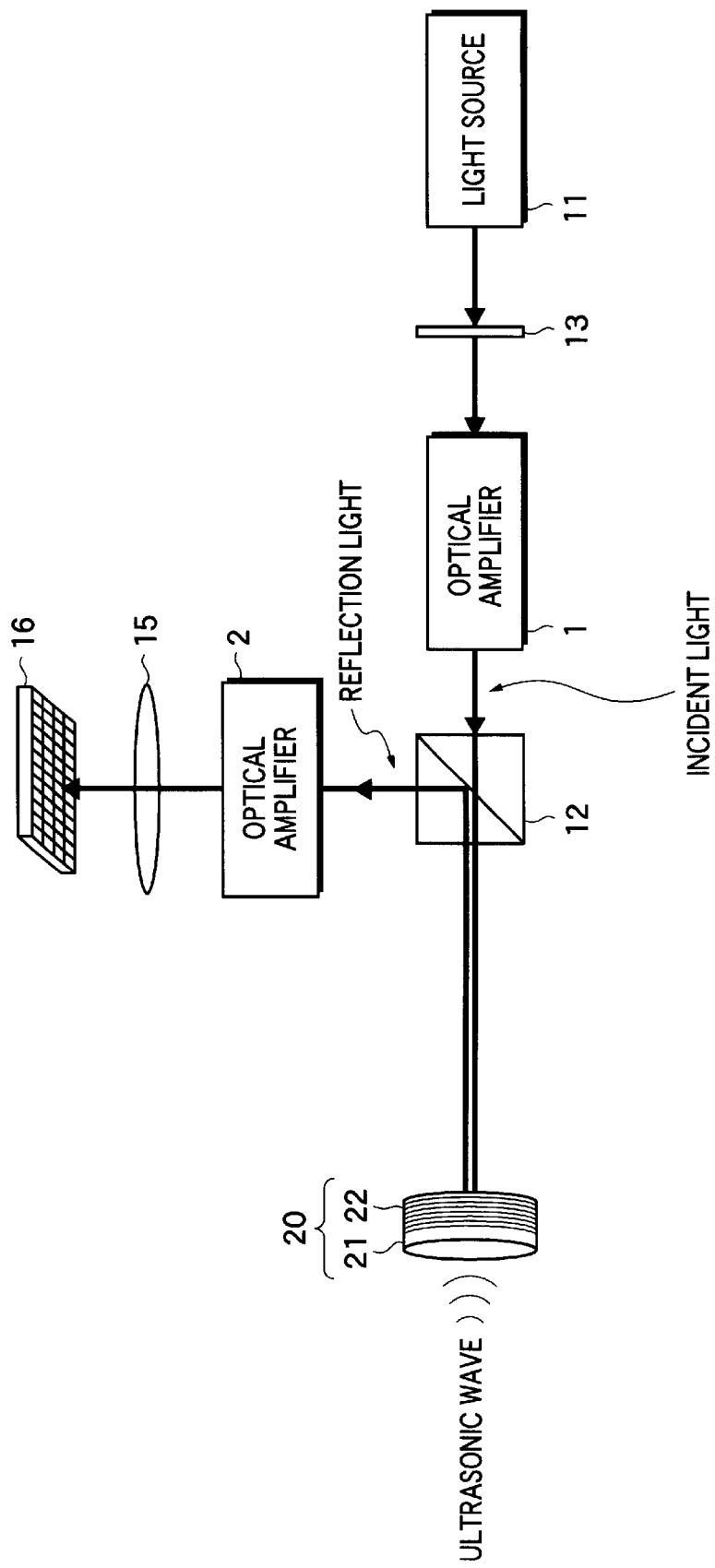
FIG. 3 is a diagram for schematically showing one modification of the ultrasonic receiving apparatus as shown in FIG. 1.

Next, a modification of the above-explained ultrasonic receiving apparatus will now be described with reference to FIG. 3.

This modified ultrasonic receiving apparatus is arranged by adding at least one of an optical amplifier 1 and another optical amplifier 2 to the ultrasonic receiving apparatus as shown in FIG. 1. The optical amplifier 1 is positioned either between the light source 11 and the beam separator 12 or between the beam expander 13 and the beam separator 12. This optical amplifier 1 optically amplifies the light entered from the light source 11, and then emits the amplified light to the beam separator 12. On the other hand, the optical amplifier 2 is positioned between the beam separator 12 and the focusing system 15 such as the lens. This optical amplifier 2 amplifies the light entered from the beam separator 12, and then emits the amplified light to the focusing system 15. In the case where this focusing system 15 is not employed, the optical amplifier 2 is positioned between the beam separator 12 and the photodetector 16, and amplifies the light entered from the beam separator 12 to emit the amplified light to the photodetector 16.

As the optical amplifier, for example, such an optical fiber amplifier EDFA (Er-doped optical fiber amplifier) is used into which erbium (Er) has been doped. This EDFA can increase intensity of light by about $10^1$ to $10^2$ times.

In the case where such an optical amplifier is positioned between the light source 11 and the ultrasonic detecting element 20, intensity of incident light which is entered into this ultrasonic detecting element 20 is amplified. Also, in the case where such an optical amplifier is arranged between the ultrasonic detecting element 20 and the photodetector 16, intensity of incident light which is entered into the ultrasonic detecting element 20 is not changed, but intensity of reflection light which is entered into the photodetector 16 is amplified. In this case, a change in the intensity of the reflection light which is modulated by the received ultrasonic waves is also amplified.

In either case, since the intensity of light is amplified, the light amount of the reflection light which is entered into the photodetector 16 is increased. As a result, an adverse influence of electric noise occurred in the photodetector 16 can be reduced, and the S/N (signal-to-noise) ratio of the ultrasonic receiving apparatus can be improved. In addition, in the case where both the optical amplifiers 1 and 2 are employed, the S/N ratio of this ultrasonic receiving apparatus can be furthermore improved.

Figure 4:
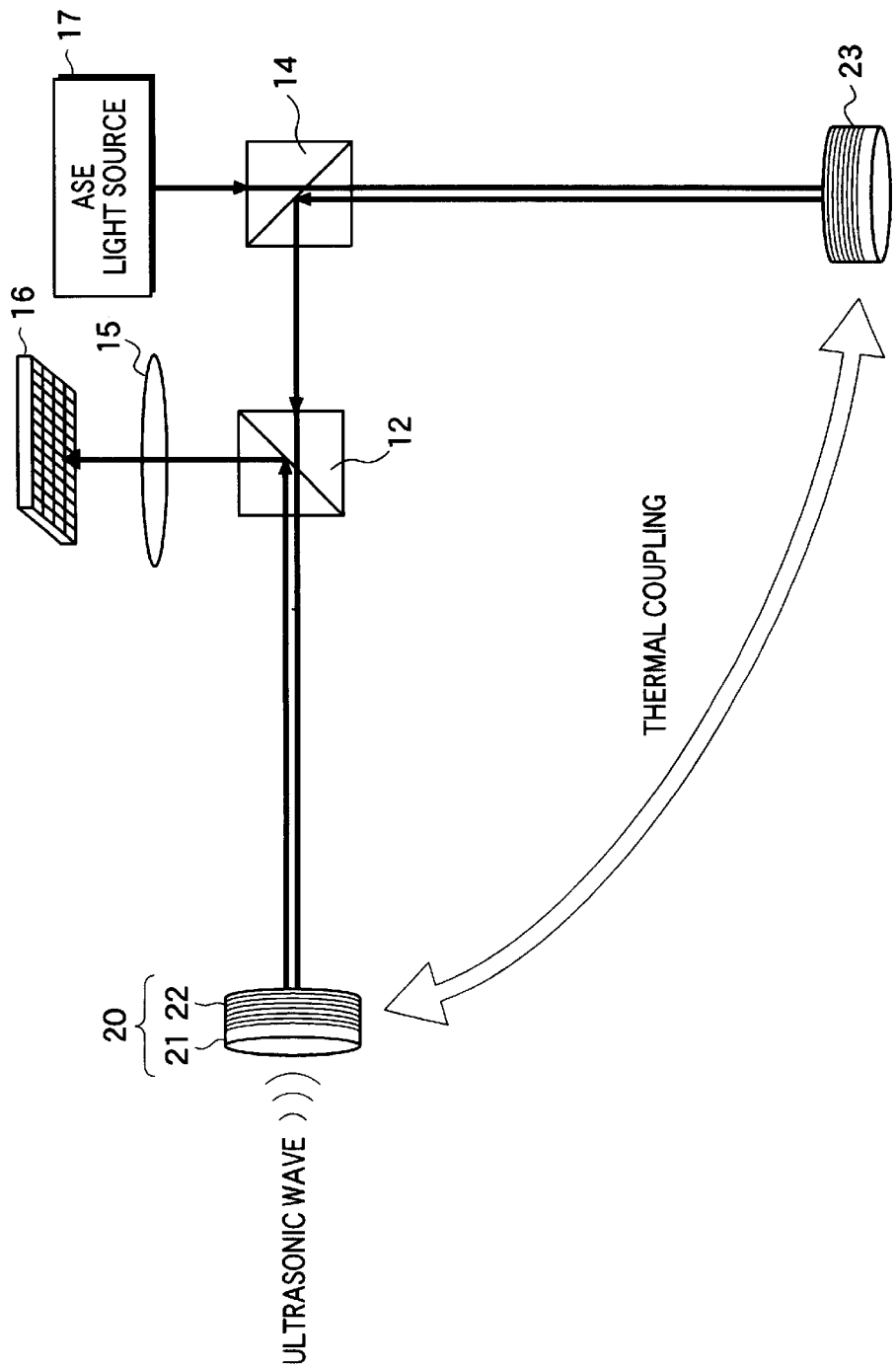
FIG. 4 is a diagram for schematically showing another modification of the ultrasonic receiving apparatus as shown in FIG. 1.

Next, another modification of the ultrasonic receiving apparatus will now be explained with reference to FIG. 4 and FIG. 5. An ultrasonic receiving apparatus as shown in FIG. 4 is realized by replacing the light source 11 of the ultrasonic receiving apparatus as shown in FIG. 1 by another light source, namely a broadband light source. In this second modified embodiment as shown in FIG. 4, a spectrum of the light which is generated from the broadband light source is narrowed by a narrow-band filter, and then, the narrow-band light is employed.

As the broadband light source, for example, an ASE (amplified spontaneous emission) light source for emitting amplified spontaneous emission light, and a broadband optical fiber light source may be employed. In FIG. 4, an ASE light source 17 is used as the broadband light source. This ASE light source 17 is realized by changing a structure of a broadband optical fiber amplifier so as to emit the amplified spontaneous emission light. The detailed structure or operation of the broadband optical fiber amplifier is described in, for example, "BROADBAND OPTICAL FIBER AMPLIFIER" written by H. OKOSHI et al. (see Japanese Electronic Information Communication Institute Publication Vol. 82, No. 7, 1999, pp. 718–724).

Figure 5:
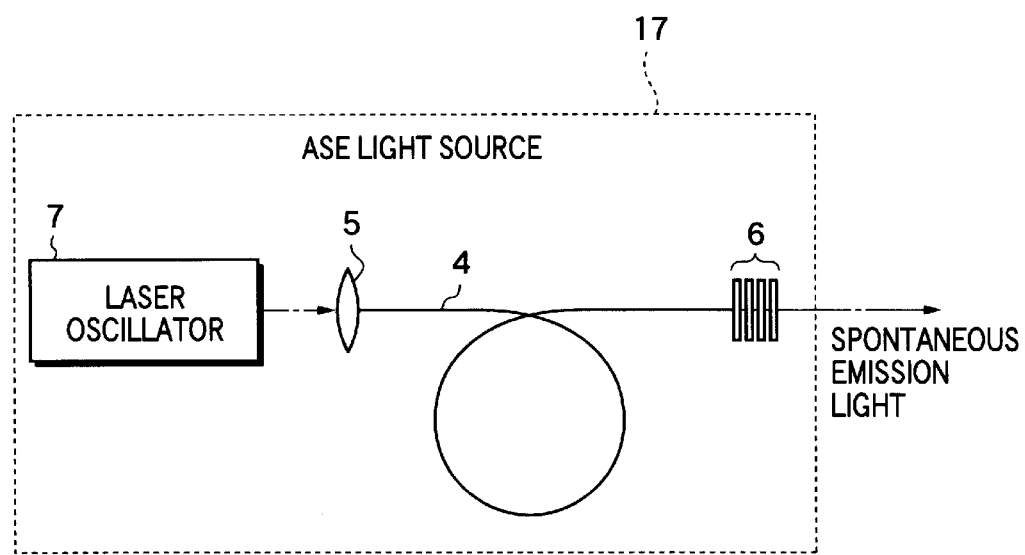
FIG. 5 is a diagram for illustratively showing a basic idea of an ASE light source as shown in FIG. 4.

Now, referring to FIG. 5, FIG. 5 illustratively shows a basic idea of the ASE light source 17 as shown in FIG. 4. This ASE light source 17 includes an optical fiber 4 for amplifying light. A lens 5 is mounted on one edge portion of this optical fiber 4, and a Bragg grating portion 6 capable of reflecting excitation light is formed on the other edge portion thereof. A laser oscillator 7 is arranged as an excitation light source on a left side of the lens 5, in this drawing. Laser light which is generated from the laser oscillator 7 is entered via the lens 5 into the optical fiber 4, and then, this entered laser light is amplified by this optical fiber 4. A portion of this amplified laser light may pass through the Bragg grating portion 6 as spontaneous emission light.

Referring back to FIG. 4, the light generated from the ASE light source 17 is entered into the beam separator 14. This beam separator 14 passes the light entered from a first direction to a second direction, and also, passes the reflection light returned from the second direction to a third direction which is different from the first direction. In FIG. 4, a half mirror is employed as the beam separator 14. Alternatively, an optical circulator or a polarization beam splitter may be employed.

In a direction (namely, lower side of FIG. 4) along which the light emitted from the ASE light source 17 passes through the beam splitter 14, a narrow-band filter 23 is provided which is made of the same material as that of the ultrasonic detecting element 20. The light which is entered into this narrow-band filter 23 is reflected by a multi-layer film having a Bragg grating structure included in the narrow-band filter 23, and then, this reflected light is again entered into the beam separator 14. The spontaneous emission light generated from the ASE light source 17 passes through the narrow-band filter 23, so that a spectrum of this spontaneous emission light can be narrowed.

The light reflected by the narrow-band filter 23 is again entered into the beam separator 14, and the propagation path of this light is changed, and then, the resultant light is entered into the beam separator 12. The light which has passed through the beam separator 12 is entered into the ultrasonic detecting element 20 so as to be modulated.

In this case, as to a Bragg grating portion, a center wavelength of reflection light is changed due to a temperature variation in a ratio of 0.01 nm/°C. As a result, when a light source for generating laser light having a single wavelength is employed, there is such a problem that the sensitivity of the ultrasonic detecting element 20 which is constituted by the Bragg grating portion is largely changed in accordance with a temperature variation.

However, when the spectrum of the spontaneous emission light generated from the ASE light source 17 is narrowed by the narrow-band filter 23 as shown in FIG. 4, a bandwidth which is approximated to that of the laser light having a single wavelength can be secured, and also, the change in the sensitivities of the ultrasonic receiving apparatus due to the temperature variation can be reduced.

That is, both the narrow-band filter 23 and the ultrasonic detecting element 20 are made by employing the same material, and thermal coupling therebetween is established by, for example, coupling the narrow-band filter 23 to the ultrasonic detecting element 20 by employing such a material having a high thermal conductivity or physically locating the narrow-band filter 23 in proximity to the ultrasonic detecting element 20. Alternatively, a heat pipe may be arranged around the narrow-band filter 23 and the ultrasonic detecting element 20.

As a consequence, since the temperature at the Bragg grating portion of the narrow-band filter 23 can be made substantially equal to the temperature at the Bragg grating portion of the ultrasonic detecting element 20, even when the reflection characteristic of the ultrasonic detecting element 20 is shifted by the temperature, the wavelength of the light which is entered into the ultrasonic detecting element 20 is similarly shifted, so that the change in the sensitivities of the ultrasonic receiving apparatus can be reduced.

Figure 6:
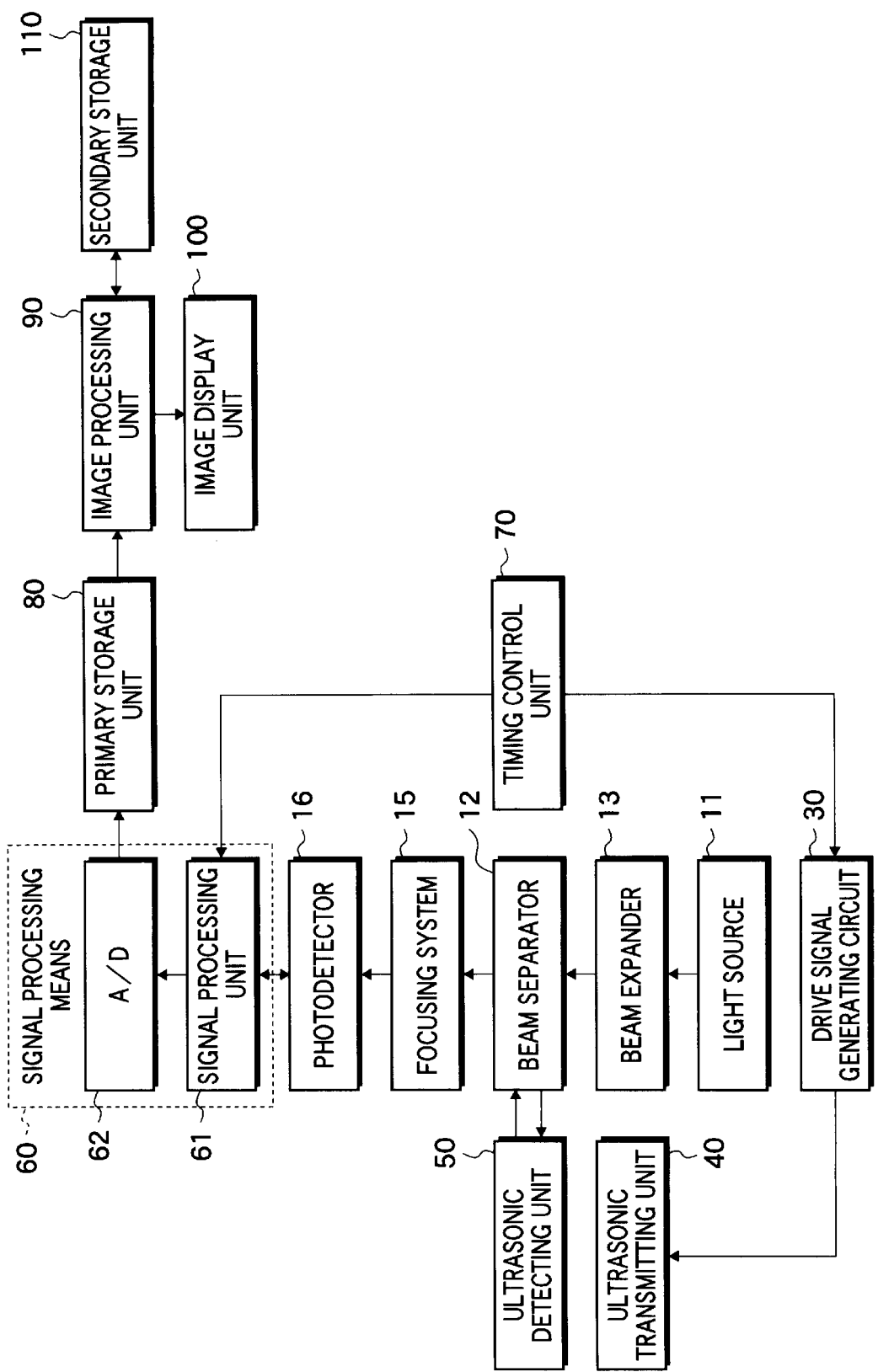
FIG. 6 is a block diagram for showing an arrangement of an ultrasonic diagnosing apparatus according to one embodiment of the present invention.

Next, an ultrasonic diagnosing apparatus according to one embodiment of the present invention will be described with referring to FIG. 6. FIG. 6 is a schematic block diagram for showing an arrangement of an ultrasonic diagnosing apparatus according to this embodiment.

This ultrasonic diagnosing apparatus is constituted by applying thereto the above-described ultrasonic receiving apparatus. That is, the ultrasonic detecting element 20 as shown in FIG. 2 is employed in an ultrasonic detecting unit 50 of this ultrasonic diagnosing apparatus. As shown in FIG. 6, this ultrasonic diagnosing apparatus includes an ultrasonic transmitting unit 40 and a drive signal generating circuit 30. The ultrasonic transmitting unit 40 transmits ultrasonic waves in accordance with drive signals generated from the drive signal generating circuit 30. The ultrasonic transmitting unit 40 includes a material (piezoelectric element) having a piezoelectric characteristic. This piezoelectric element is realized by piezoelectric ceramics which is typically known as PZT (Pb (lead) zirconate titanate), or a polymer piezoelectric element such as PVDF (polyvinyl difluoride). When either a pulse-shaped electric signal or a continuous-wave (CW) electric signal is transmitted from the drive signal generating circuit 30 so as to apply a voltage to such a piezoelectric element, this piezoelectric element produces very small mechanical vibrations. Since such mechanical vibrations are produced, either ultrasonic pulses or continuous-wave (CW) ultrasonic waves are generated from this piezoelectric element, and then, are propagated as ultrasonic beams through a propagation medium.

The ultrasonic waves transmitted from the ultrasonic transmitting unit 40 are reflected from a diagnostic object, and then, the reflected ultrasonic waves (namely, ultrasonic echoes) are received by the ultrasonic detecting unit 50. While the light which has been generated from the light source and has passed through the beam separator 12 is entered into the ultrasonic detecting unit 50, this light is modulated on the basis of the ultrasonic beams applied to the ultrasonic detecting unit 50, and then, this modulated light is reflected from this ultrasonic detecting unit 50. The reflected light is entered via the beam separator 12 and the focusing system 15 into the photodetector 16 so as to be detected in a two-dimensional manner.

This ultrasonic diagnosing apparatus further includes a signal processing means 60 including both a signal processing unit 61 and an A/D converter 62, a timing control unit 70, a primary storage unit 80, an image processing unit 90, an image display unit 100, and a secondary storage unit 110.

In the signal processing means 60, a detection signal output from the photodetector 16 is entered into a signal processing unit 61, and the detection signal processed by the signal processing unit 61 is converted into a digital signal in the A/D converter 62.

The primary storage unit 80 stores thereinto plural sheets of plane data acquired by the signal processing means 60. The image processing unit 90 reconstructs either two-dimensional data or three-dimensional data on the basis of these plane data, and also, executes such process operations as an interpolation process, a response modulation process, and a gradation process. The image display unit 100 corresponds to a display apparatus such as a CRT or an LCD, for example, and displays thereon an image on the basis of the image data to which these process operations have been carried out. Further, the secondary storage unit 110 stores thereinto data which has been processed by the image processing unit 90.

The timing control unit 70 controls the drive signal generating unit 30 to generate the drive signal at predetermined timing, and also controls the signal processing unit 61 to acquire detection signals from the photodetector 16 after a predetermined time period has passed from a transmission time instant. Thus, the timing control unit 70 controls both timing of the drive signal and timing of the detection signal so as to limit a readout time range, so that reflections of ultrasonic waves from a specific depth of an object to be inspected can be optically detected.

Figure 7:
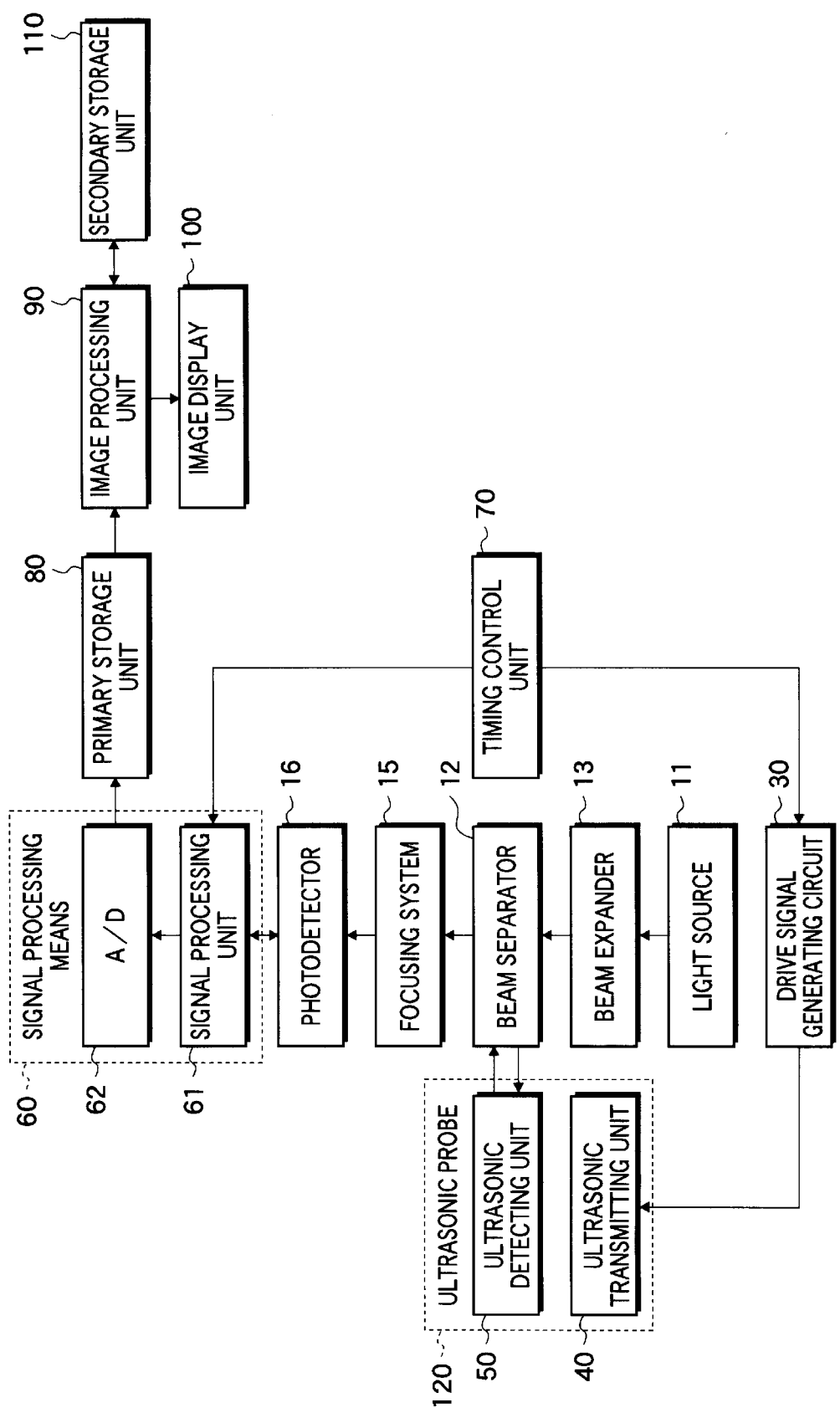
FIG. 7 is a block diagram for showing an arrangement of one modification of an ultrasonic diagnosing apparatus as shown in FIG. 6.

Next, a description will now be made of a modification of the ultrasonic diagnosing apparatus according to this embodiment with reference to FIG. 7. As shown in FIG. 7, in this modified ultrasonic diagnosing apparatus, both the ultrasonic detecting unit 50 and the ultrasonic transmitting unit 40 are formed in an integral manner, so that an ultrasonic probe 120 is formed.

Since an optical detecting type ultrasonic detector does not own a function of transmitting ultrasonic waves, such an ultrasonic transmitting unit using a piezoelectric element must be separately provided. As to the modification as shown in FIG. 7, since both the ultrasonic transmitting unit and the ultrasonic detecting unit, which employ the different systems, are combined with each other to form a single probe. This modified ultrasonic diagnosing apparatus is capable of performing the ultrasonic diagnosing operation, while having a similar operation feeling as that of the conventional probe with employment of the same transmission/reception system.

In the ultrasonic diagnosing apparatus as shown in FIG. 6 and FIG. 7, the below-mentioned three sorts of transmission methods of ultrasonic waves may be conceived in the drive signal generating circuit 30 and the ultrasonic transmitting unit 40. In response to these ultrasonic wave transmission methods, data acquisition time instants and contents of data in the signal processing unit 61 are changed.

Figure 8:
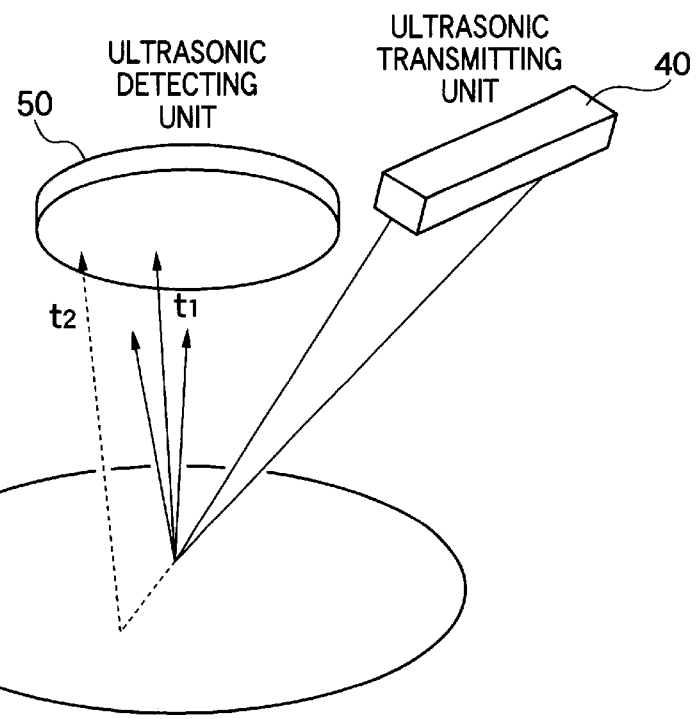
FIG. 8 is a diagram for explaining a reception method executed in the case where ultrasonic beams are limited into a pencil beam and this pencil beam is transmitted.

(1) In the case where ultrasonic waves are limited to form a pencil-beam-shaped ultrasonic beam, and then, this pencil-beam-shaped ultrasonic beam is transmitted:

As shown in FIG. 8, if transmission waves are spatially limited to form a pencil-beam-shaped ultrasonic beam by the ultrasonic transmitting unit 40, an object to be inspected is scanned within a certain plane in the two-dimensional manner, and then, detection signals of ultrasonic echoes which have been received after a predetermined time period has elapsed from a transmission thereof is acquired by the ultrasonic detecting unit 50, ultrasonic information at the respective points on this plane can be acquired. When this operation is carried out within a sectional view which is located at a constant depth from the ultrasonic detecting unit 50, sectional plane information at a constant depth can be acquired. When a series of the above-described processing steps are repeatedly carried out by changing the acquisition time at each of the pencil beam positions, a plurality of tomographic images at different depths can be acquired. The sample data which have been acquired in the above-described manner are focused both in the transmission/reception operations, and therefore, may be directly displayed as three-dimensional data.

Figure 9:
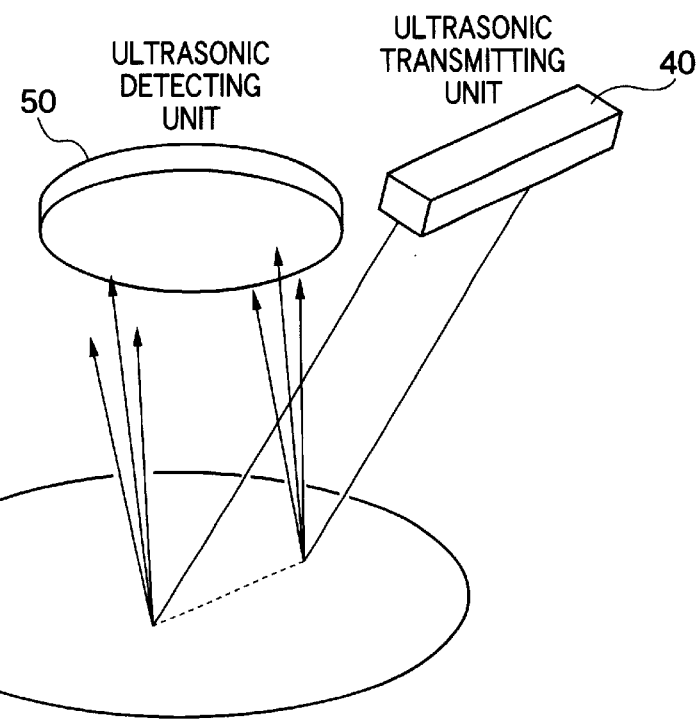
FIG. 9 is a diagram for explaining a reception method executed in the case where ultrasonic beams are limited to a plane-shaped beam and this plane-shaped beam is transmitted.

(2) In the case where ultrasonic waves are limited to form a plane-shaped ultrasonic wave, and then, this plane-shaped ultrasonic wave is transmitted:

Also, as shown in FIG. 9, if the transmission ultrasonic waves generated from the ultrasonic transmitting unit 40 are limited to form a plane-shaped ultrasonic wave by using an acoustic lens, and also detection signals of ultrasonic echoes which have been received after a predetermined time period has elapsed from the transmission of the ultrasonic transmission waves are acquired by the ultrasonic detecting unit 50, then one-dimensional line information of a certain depth can be acquired in a batch manner. In this case, since information of other points in the region to which the ultrasonic waves are applied is also mixed with the information as to the respective points, it would be necessary to carry out the wave-front synthesizing operation (so-called "aperture synthesizing operation") on the basis of the detection signals, the acquisition time instants of which are shifted, and then, to reconstruct the data where focal points are coincident with each other so as to obtain a display image.

Figure 10:
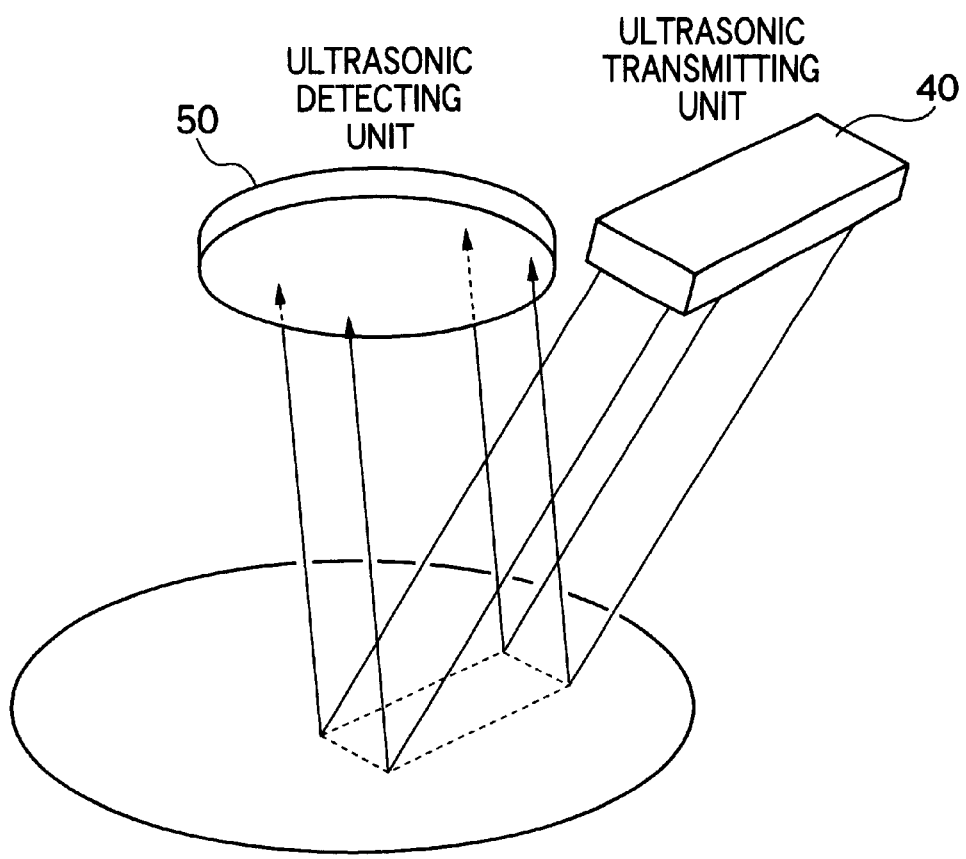
FIG. 10 is a diagram for explaining a reception method executed in the case where ultrasonic beams are transmitted as plane waves.

(3) In the case where ultrasonic waves are transmitted as plane waves:

Furthermore, as shown in FIG. 10, if the transmission ultrasonic waves are transmitted as a plane-shaped wave from the ultrasonic transmitting unit 40, and also detection signals of ultrasonic echoes which have been received after a predetermined time period has elapsed from the transmission of the ultrasonic waves are acquired by the ultrasonic detecting unit 50, then two-dimensional plane information at a certain depth can be acquired in a batch manner. When this process step is repeatedly carried out while the acquisition time is changed, a plurality of tomographic images at the different depths can be acquired. In this case, since information of other points in the region to which the ultrasonic waves are applied is also mixed with the information as to the respective points, it would be necessary to carry out the wave-front synthesizing operation (so-called "aperture synthesizing operation") on the basis of the detection signals, the acquisition time instants of which are shifted, and then, to reconstruct the data where focal points are coincident with each other so as to obtain a display image.

As previously described in detail, in accordance with the present invention, since an ultrasonic detecting element having an ultrasonic receiving plane corresponding to a plurality of pixels of a photodetector is employed, ultrasonic waves can be detected in a two-dimensional manner. Such an ultrasonic detecting element can be manufactured in low cost, as compared with a case where a plurality of fiber Bragg gratings are formed into an array. As a result, the manufacturing cost of the ultrasonic receiving apparatus can be lowered. Also, layers of a multi-layer film as the ultrasonic detecting element are formed one by one in the vapor deposition method, the sputtering method or the like, a plurality of materials having largely different refractive indexes can be selected. As a consequence, inclination of the reflectance can be increased, and the sensitivity of the ultrasonic receiving apparatus can be improved. By using the ultrasonic diagnosing apparatus which employs such an ultrasonic receiving apparatus, either two-dimensional or three-dimensional ultrasonic images having better qualities can be acquired.

What is claimed is:

1. An ultrasonic receiving apparatus comprising:
   an ultrasonic detecting element having a reception plane capable of receiving ultrasonic waves and an ultrasonic sensing portion which is expanded and contracted by ultrasonic waves received at respective positions of said reception plane to change optical reflections at corresponding positions of said ultrasonic sensing portion in accordance with expansion and contraction, thereby modulating light on the basis of ultrasonic waves received at the respective positions of said reception plane; and
   a photodetector having a plurality of pixels, for detecting light output from corresponding positions of said ultrasonic detecting element.

2. An ultrasonic receiving apparatus according to claim 1, wherein:
   said photodetector includes any one of a CCD (charge-coupled device), an MOS (metal oxide semiconductor) type sensor, and a plurality of photodiodes.

3. An ultrasonic receiving apparatus according to claim 1, further comprising:
   a beam expander for expanding light generated from a light source.

4. An ultrasonic receiving apparatus according to claim 1, further comprising:
   an optical amplifier for amplifying light generated from a light source to enter the amplified light into said ultrasonic detecting element.

5. An ultrasonic receiving apparatus according to claim 1, further comprising:
   an optical amplifier for amplifying light output from said ultrasonic detecting element to enter the amplified light into said photodetector.

6. An ultrasonic receiving apparatus according to claim 1, further comprising:
   a light source for generating single-mode laser light having a wavelength of 500 nm to 1,600 nm.

7. An ultrasonic receiving apparatus comprising:
   an ultrasonic detecting element having a reception plane capable of receiving ultrasonic waves, for modulating light on the basis of ultrasonic waves received at respective positions of said reception plane; and
   a photodetector having a plurality of pixels, for detecting light output from corresponding positions of said ultrasonic detecting element, wherein:
   said ultrasonic detecting element includes a multi-layer film formed by alternately stacking two sorts of materials having different refractive indexes from each other.

8. An ultrasonic receiving apparatus according to claim 7, wherein:
   said two sorts of materials have refractive indexes which are different from each other by at least 10%.

9. An ultrasonic receiving apparatus according to claim 7, wherein:
   layers of said two sorts of materials which constitute said multi-layer film include a layer having a film thickness of substantially ¼ of a wavelength of light entered into said multi-layer film.

10. An ultrasonic receiving apparatus according to claim 8, wherein:
    layers of said two sorts of materials which constitute said multi-layer film include a layer having a film thickness of substantially ¼ of a wavelength of light entered into said multi-layer film.

11. An ultrasonic receiving apparatus according to claim 9, wherein:
    layers of said two sorts of materials which constitute said multi-layer film further include a layer having a film thickness of substantially ½ of a wavelength of light entered into said multi-layer film.

12. An ultrasonic receiving apparatus according to claim 10, wherein:
    layers of said two sorts of materials which constitute said multi-layer film further include a layer having a film thickness of substantially ½ of a wavelength of light entered into said multi-layer film.

13. An ultrasonic receiving apparatus comprising:
    an ultrasonic detecting element having a reception plane capable of receiving ultrasonic waves, for modulating light on the basis of ultrasonic waves received at respective positions of said reception plane; and
    a photodetector having a plurality of pixels, for detecting light output from corresponding positions of said ultrasonic detecting element;
    further comprising:
    a broadband light source; and
    a narrow-band filter for narrowing a spectrum of light generated from said broadband light source.

14. An ultrasonic receiving apparatus according to claim 13, wherein:
    said broadband light source includes an ASE (amplified spontaneous emission) light source for emitting amplified spontaneous emission light.

15. An ultrasonic receiving apparatus according to claim 13, wherein:
    said narrow-band filter has a Bragg grating structure constituted by using the same material as that of a Bragg grating structure of said ultrasonic detecting element; and
    the Bragg grating structure of said narrow-band filter is thermally coupled to the Bragg grating structure of said ultrasonic detecting element.

16. An ultrasonic diagnosing apparatus comprising:
    a drive signal generating circuit for generating drive signals;
    transmission means for transmitting ultrasonic waves in response to the drive signals;
    reception means including an ultrasonic detecting element and a photodetector, said ultrasonic detecting element having a reception plane capable of receiving ultrasonic waves and modulating light on the basis of ultrasonic waves applied to respective positions of said reception plane, said photodetector having a plurality of pixels and detecting light output from corresponding positions of said ultrasonic detecting element to thereby output detection signals;

signal processing means for receiving the detection signals output from said reception means to process the received detection signals;

control means for controlling both generation timing of the drive signals and acquisition timing of the detection signals;

image processing means for constructing image data on the basis of an output signal of said signal processing means; and an image display unit for displaying thereon an image on the basis of the image data.

17. An ultrasonic diagnosing apparatus according to claim 16, wherein:

said transmission means belongs to a piezoelectric type ultrasonic transmission means for generating ultrasonic waves in response to voltage applied thereto.

18. An ultrasonic diagnosing apparatus according to claim 16, wherein:

said ultrasonic detecting element includes a multi-layer film formed by alternately stacking two sorts of materials having different refractive indexes from each other.

19. An ultrasonic diagnosing apparatus according to claim 18, wherein:

said two sorts of materials have refractive indexes which are different from each other by not less than 10%.

20. An ultrasonic diagnosing apparatus according to claim 18, wherein:

layers of said two sorts of materials which constitute said multi-layer film include a layer having a film thickness of substantially ¼ of a wavelength of light entered into said multi-layer film.

21. An ultrasonic diagnosing apparatus according to claim 19, wherein:

layers of said two sorts of materials which constitute said multi-layer film include a layer having a film thickness of substantially 1/4 of a wavelength of light entered into said multi-layer film.

22. An ultrasonic diagnosing apparatus according to claim 20, wherein:

layers of said two sorts of materials which constitute said multi-layer film further include a layer having a film thickness of substantially ½ of a wavelength of light entered into said multi-layer film.

23. An ultrasonic diagnosing apparatus according to claim 21, wherein:

layers of said two sorts of materials which constitute said multi-layer film further include a layer having a film thickness of substantially ½ of a wavelength of light entered into said multi-layer film.

24. An ultrasonic diagnosing apparatus according to claim 16, wherein:

both said transmission means and said ultrasonic detecting element included in said detection means are formed in an integral shape to thereby constitute an ultrasonic wave probe.

* * * * *